US012727988B2

(12) United States Patent
Braeuer et al.

(10) Patent No.: US 12,727,988 B2
(45) Date of Patent: Sep. 8, 2026

(54) TIPS STENT GRAFT AND KIT COMPRISING TIPS STENT GRAFT

(71) Applicant: Angiomed GmbH & Co. Medizintechnik KG, Karlsruhe (DE)

(72) Inventors: Pia Ute Braeuer, Königsbach-Stein (DE); Amal Belkouch, Karlsruhe (DE)

(73) Assignee: Angiomed GmbH & Co. Medizintechnik KG, Karlsruhe (DE)

(*) Notice: Subject to any disclaimer, the term of this patent is extended or adjusted under 35 U.S.C. 154(b) by 554 days.

(21) Appl. No.: 17/773,484

(22) PCT Filed: Oct. 30, 2019

(86) PCT No.: PCT/EP2019/079639
§ 371 (c)(1),
(2) Date: Apr. 29, 2022

(87) PCT Pub. No.: WO2021/083506
PCT Pub. Date: May 6, 2021

(65) Prior Publication Data
US 2024/0164887 A1 May 23, 2024

(51) Int. Cl.
*A61F 2/07* (2013.01)
*A61B 17/12* (2006.01)
(Continued)

(52) U.S. Cl.
CPC .......... *A61F 2/07* (2013.01); *A61B 17/12036* (2013.01); *A61B 17/1204* (2013.01);
(Continued)

(58) Field of Classification Search
CPC ...... A61F 2/07; A61F 2/958; A61F 2002/061; A61F 2002/068; A61F 2002/072;
(Continued)

(56) References Cited

U.S. PATENT DOCUMENTS 4,773,431 A 9/1988 Lodomirski
4,808,157 A 2/1989 Coombs
(Continued)

FOREIGN PATENT DOCUMENTS

CN 107073723 A 8/2017
CN 107374702 A 11/2017
(Continued)

OTHER PUBLICATIONS

Bilbao, J., Elorz, M., Vivas, I. et al. Transjugular Intrahepatic Portosystemic Shunt (TIPS) in the Treatment of Venous Symptomatic Chronic Portal Thrombosis in Non-cirrhotic Patients. CVIR 27, 47 4-480 (2004). https://doi.org/10.1007/s00270-004-0241-z (Year: 2004).

(Continued)

*Primary Examiner* — Rebecca E Eisenberg
*Assistant Examiner* — Timothy L Flynn
(74) *Attorney, Agent, or Firm* — Rutan & Tucker LLP

(57) ABSTRACT

The invention relates to a TIPS stent graft, comprising: a hollow stent graft body, the stent body having a lumen extending between a first longitudinal end and a second longitudinal end to let fluid pass through the stent graft body from the first longitudinal end to the second longitudinal end, the lumen comprising at least two sublumens which are separated from one another, each of the sublumens extending from the first longitudinal end to the second longitudinal end, each of the sublumens being capable of being blocked so as to reduce blood flow through the TIPS stent graft.

18 Claims, 1 Drawing Sheet

(51) Int. Cl.

| | |
|---|---|
| ***A61F 2/06*** | (2013.01) |
| ***A61F 2/958*** | (2013.01) |
| ***A61M 27/00*** | (2006.01) |

(52) U.S. Cl.

CPC ........ *A61F 2/958* (2013.01); *A61F 2002/061* (2013.01); *A61F 2002/068* (2013.01); *A61M 27/002* (2013.01); *A61M 2210/1071* (2013.01)

(58) Field of Classification Search

CPC ........ A61F 2210/0076; A61F 2250/001; A61F 2250/0013; A61F 2250/0069; A61B 17/12036; A61B 17/1204; A61M 27/002; A61M 2210/1071

See application file for complete search history.

(56) References Cited

U.S. PATENT DOCUMENTS

| | | | |
|---|---|---|---|
| 4,958,901 | A | 9/1990 | Coombs |
| 5,360,409 | A | 11/1994 | Boyd, III et al. |
| 5,441,483 | A | 8/1995 | Avitall |
| 5,848,986 | A | 12/1998 | Lundquist et al. |
| 6,093,173 | A | 7/2000 | Balceta et al. |
| 6,117,112 | A | 9/2000 | Mahurkar |
| 6,171,303 | B1 | 1/2001 | Ben-Haim et al. |
| 7,867,219 | B2 | 1/2011 | Chambers |
| 8,287,481 | B1 | 10/2012 | Kahn et al. |
| 9,901,675 | B2 | 2/2018 | Ella et al. |
| 10,638,964 | B2 | 5/2020 | Lampropoulos et al. |
| 2002/0082584 | A1 | 6/2002 | Rosenman et al. |
| 2002/0173751 | A1 | 11/2002 | Mastorakis |
| 2003/0167068 | A1 | 9/2003 | Amplatz |
| 2004/0111101 | A1 | 6/2004 | Chin |
| 2005/0165466 | A1 | 7/2005 | Morris et al. |
| 2006/0259061 | A1 | 11/2006 | Kick et al. |
| 2007/0129719 | A1 | 6/2007 | Kendale et al. |
| 2007/0191773 | A1 | 8/2007 | Wojcik |
| 2007/0239119 | A1 | 10/2007 | Lipov |
| 2008/0109066 | A1* | 5/2008 | Quinn ........................ A61F 2/07 623/1.13 |
| 2009/0177041 | A1 | 7/2009 | Stefanchik et al. |
| 2010/0106093 | A1 | 4/2010 | McGuckin, Jr. et al. |
| 2010/0152665 | A1 | 6/2010 | Hasted |
| 2010/0256730 | A1 | 10/2010 | Berglund |
| 2011/0137125 | A1 | 6/2011 | Belsley |
| 2011/0152741 | A1 | 6/2011 | Banchieri et al. |
| 2011/0202067 | A1 | 8/2011 | Falkner et al. |
| 2011/0213316 | A1 | 9/2011 | Ibrahim et al. |
| 2012/0221007 | A1 | 8/2012 | Batten et al. |
| 2013/0245533 | A1 | 9/2013 | Kahn et al. |
| 2014/0114330 | A1 | 4/2014 | Karasic et al. |
| 2014/0171826 | A1 | 6/2014 | Lampropoulos et al. |
| 2015/0032141 | A1 | 1/2015 | Silvestro |
| 2015/0045769 | A1 | 2/2015 | Cabrera Aquino et al. |
| 2015/0297246 | A1 | 10/2015 | Patel et al. |
| 2016/0106971 | A1 | 4/2016 | Servin De La Mora Godinez et al. |
| 2016/0331443 | A1 | 11/2016 | Phan et al. |
| 2016/0361088 | A1 | 12/2016 | Maguire et al. |
| 2017/0042551 | A1 | 2/2017 | Celermajer et al. |
| 2017/0049511 | A1 | 2/2017 | Uhm et al. |
| 2017/0071769 | A1* | 3/2017 | Mangiardi .............. A61F 2/844 |
| 2017/0325930 | A1* | 11/2017 | Montgomery ............ A61F 2/01 |
| 2017/0367855 | A1* | 12/2017 | Jenni ......................... A61F 2/07 |
| 2018/0207406 | A1 | 7/2018 | Ishida |
| 2018/0256021 | A1 | 9/2018 | Gill |
| 2018/0256223 | A1 | 9/2018 | Lueth et al. |
| 2018/0344985 | A1 | 12/2018 | Shah et al. |
| 2019/0117937 | A1 | 4/2019 | Humphrey et al. |
| 2019/0184136 | A1 | 6/2019 | Lubinski et al. |
| 2019/0282217 | A1 | 9/2019 | Graham et al. |
| 2019/0282218 | A1 | 9/2019 | Panzenbeck et al. |
| 2021/0128873 | A1 | 5/2021 | Scott et al. |
| 2021/0282950 | A1* | 9/2021 | MacTaggart ....... A61B 5/14539 |
| 2022/0105316 | A1 | 4/2022 | Lutz |
| 2022/0211413 | A1 | 7/2022 | Yi et al. |
| 2022/0240981 | A1 | 8/2022 | Yi et al. |
| 2022/0241562 | A1 | 8/2022 | Yi et al. |
| 2024/0225692 | A1 | 7/2024 | Forreiter |

FOREIGN PATENT DOCUMENTS

| | | | |
|---|---|---|---|
| CN | 107412935 | A | 12/2017 |
| CN | 107661552 | A | 2/2018 |
| CN | 108618739 | A | 10/2018 |
| WO | 9724983 | A2 | 7/1997 |
| WO | 9856293 | A1 | 12/1998 |
| WO | 03028522 | A2 | 4/2003 |
| WO | 2008014791 | A1 | 2/2008 |
| WO | 2008121888 | A1 | 10/2008 |
| WO | 2010115134 | A1 | 10/2010 |
| WO | 14071161 | A1 | 5/2014 |
| WO | 14100349 | A1 | 6/2014 |
| WO | 2018022432 | A1 | 2/2018 |
| WO | 18112118 | A1 | 6/2018 |
| WO | 2020237420 | A1 | 12/2020 |
| WO | 2022242874 | A1 | 11/2022 |

OTHER PUBLICATIONS

EP 19930992.3 filed Nov. 24, 2021 Extended European Search Report dated Oct. 18, 2022.

EP 199310871 filed Nov. 24, 2021 Extended European Search Report dated Nov. 3, 2022.

PCT/CN2019/088318 filed May 24, 2019 International Search Report and Written Opinion dated Feb. 6, 2020.

PCT/CN2019/088334 filed May 24, 2019 International Search Report and Written Opinion dated Feb. 6, 2020.

PCT/CN2019/088347 filed May 24, 2019 International Search Report and Written Opinion dated Feb. 12, 2020.

PCT/EP2021/063619 filed May 21, 2021 International Search Report and Written Opinion dated Feb. 14, 2022.

U.S. Appl. No. 17/612,188 filed Nov. 17, 2021 Final Office Action dated May 19, 2025.

U.S. Appl. No. 17/612,188 filed Nov. 17, 2021 Final Office Action dated Oct. 1, 2024.

U.S. Appl. No. 17/612,188 filed Nov. 17, 2021 Non-Final Office Action dated Jun. 20, 2024.

U.S. Appl. No. 17/612,188 filed Nov. 17, 2021 Non-Final Office Action dated Nov. 25, 2024.

U.S. Appl. No. 17/612,189 filed Nov. 17, 2021 Final Office Action dated Dec. 17, 2024.

U.S. Appl. No. 17/612,189 filed Nov. 17, 2021 Non-Final Office Action dated Jul. 25, 2024.

U.S. Appl. No. 17/612,189, filed Nov. 17, 2021 Notice of Allowance dated Mar. 13, 2025.

U.S. Appl. No. 17/612,196 filed Nov. 17, 2021 Non-Final Office Action dated Nov. 19, 2024.

U.S. Appl. No. 17/612,188 filed Nov. 17, 2021 Advisory Action dated Jul. 28, 2025.

U.S. Appl. No. 18/561,980, filed Nov. 17, 2023 Non-Final Office Action dated Jun. 9, 2025.

U.S. Appl. No. 17/612,188 filed Nov. 17, 2021 Examiner's Answer dated Dec. 29, 2025.

U.S. Appl. No. 17/612,196 filed Nov. 17, 2021 Non-Final Office Action dated Nov. 14, 2025.

U.S. Appl. No. 18/561,980, filed Nov. 17, 2023 Final Office Action dated Jan. 26, 2026.

* cited by examiner

Fig.1
a) 10 18 17 12 14 16
b) 36 18 16
c) 36 40 18 16
Fig.2
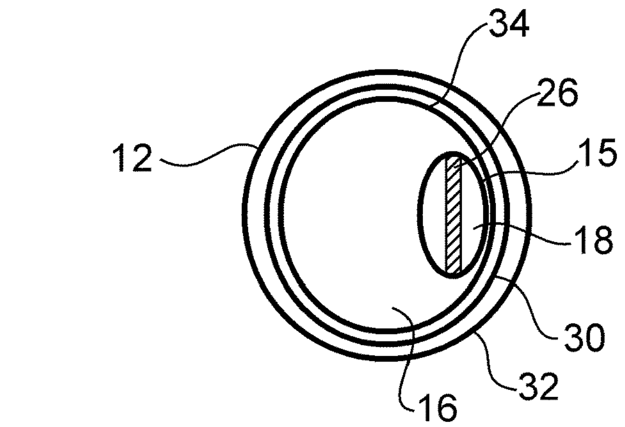
Fig.3
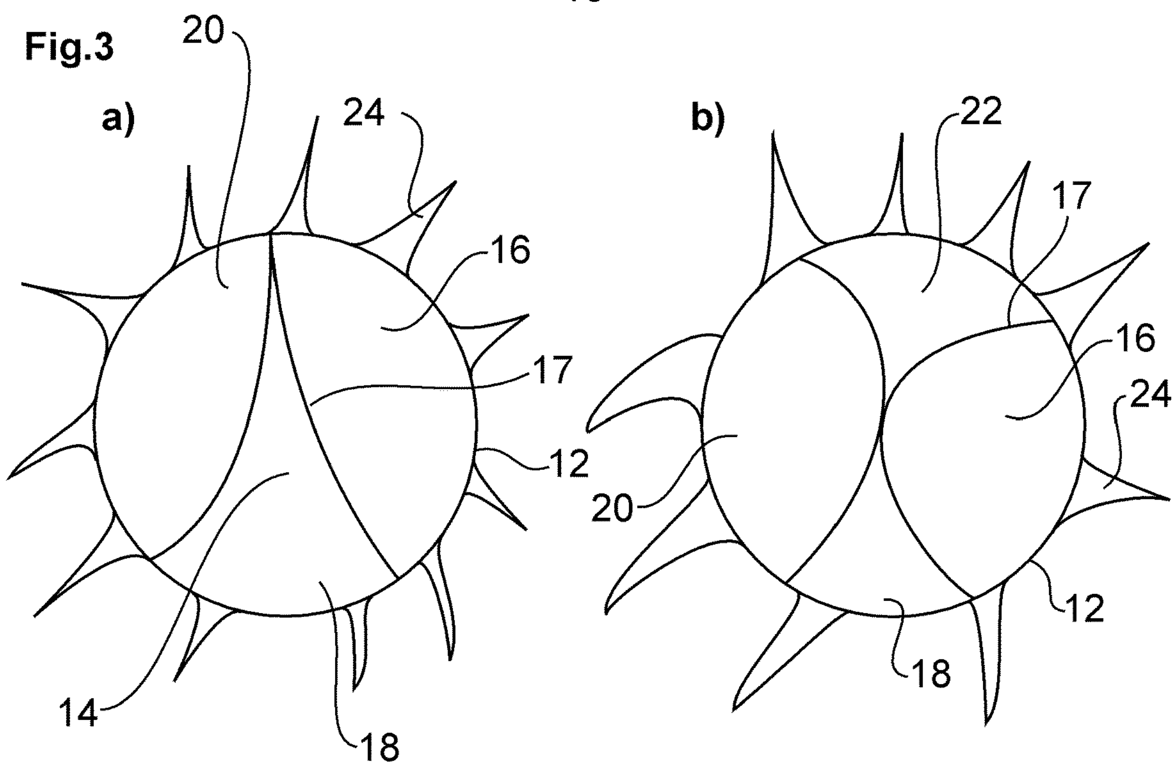

TIPS STENT GRAFT AND KIT COMPRISING TIPS STENT GRAFT

PRIORITY

This application is a U.S. national stage application of International Application No. PCT/EP2019/079639, filed Oct. 30, 2019, which is incorporated by reference in its entirety into this application.

TECHNICAL FIELD

The present invention relates to a TIPS stent graft, i.e. stent grafts for use in a transjugular intrahepatic portosystematic shunt (TIPS).

TECHNICAL BACKGROUND

Portal hypertension is a medical condition which often occurs in patients suffering from liver cirrhosis and is a hypertension (high blood pressure) in the hepatic portal system that is made up of the portal vein and its branches that drain from most of the intestine to the liver.

Portal hypertension leads to a number of other conditions such as ascites, gastrointestinal bleeding, hepatic encephalopathy, varices, and splenomegaly which severely affect a patient's wellbeing and prognosis. In particular, varices can lead to sudden bleeding and death. Accordingly, portal hypertension needs to be treated.

In order to treat patients having portal hypertension, a transjugular intrahepatic portosystematic shunt (TIPS) is frequently used. Such a shunt is an artificial channel through the liver which extends between the portal vein and the hepatic vein. Through that shunt, blood can flow and can "bypass" the liver, which reduces the blood pressure the liver is exposed to, so that the portal hypertension is reduced. In turn, this alleviates the conditions mentioned above and, accordingly, improves patient wellbeing and his or her prognosis.

It is, however, clear that the cross-sectional area of the TIPS shunt needs to be accurately adjusted—if the area is too small, hardly any blood will flow through it, so that the shunt does not have the intended effect of reducing portal hypertension. If the area is too large, too much blood will flow through the shunt so that the blood is not adequately filtered by the liver, which has negative effects on the patient's health and can, in the case of between 20% and 30% of the patients, lead to hepatic encephalopathy, which leads to a loss of cognitive function, personality changes, lethargy and depressed consciousness.

In this respect, it is to be noted that sometimes, a TIPS stent graft will widen during use, so that a once appropriately adjusted TIPS stent graft will, during use, expand and thus be less than optimal in its function. Additionally, with modern TIPS stent grafts, one can, if desired, increase the TIPS stent graft diameter by means of introducing a balloon and expanding it—however, a reduction of the cross-sectional area is, unfortunately, not possible with prior art TIPS stent grafts.

SUMMARY OF THE INVENTION

The inventors have realised that it would be advantageous to provide a TIPS stent graft which avoids the above complications by having a cross-sectional area which can be reduced.

The invention is defined by the TIPS stent graft according to claim 1 and by the kit of parts as defined in claim 9. Preferred embodiments are defined in the respective dependent claims.

According to the invention, a TIPS stent graft, that is, a stent graft intended for use in a TIPS procedure, comprises a hollow stent graft body. This stent graft body is formed of a covered stent, that is, a stent which is coated with a coating material such as, for example, ePTFE. However, FEP would also be an option. The stent graft body has a lumen which extends between a first longitudinal end and a second longitudinal end of the stent graft body to let a fluid pass through that stent graft body from the first longitudinal end to the second longitudinal end. The stent graft may have, at one of its longitudinal ends, uncovered stent parts (i.e. the stent graft body leads onto a bare stent component which does not have a graft material. The stent component can be arranged to flare out when implanted in the body, with the flare holding the TIPS stent graft inside the portal vein.

The stent graft body has its lumen separated into at least two sublumens. Those sublumens can be separated from each other by a membrane which could also be made of the covering material of the stent graft body. Both of these sublumens extend from the first longitudinal end to the second longitudinal end of the stent graft body. At least one of these sublumens is capable of being blocked by a specific occlusion device (e.g. am embolization coil) so as to not allow or significantly reduce blood flow through the blocked lumen.

By subdividing the lumen of the stent graft body into two sublumens, it becomes possible, if desired, to reduce the blood flow through those lumens by means of blocking one of them. Thereby, one can, if it becomes evident that the patient is suffering from hepatic encephalopathy, block one of those sublumens. This will then reduce the flow through the TIPS stent graft which will, in turn, alleviate hepatic encephalopathy. Whilst for the blockage of the stent graft, a separate occlusion device is needed, a TIPS stent graft as such already provides the advantage of having the capability of being partially occluded. In the case of a normal TIPS stent graft without the separated lumen of the stent graft body, this would not be possible, since one could, at best, prevent blood flow through the entire TIPS stent graft.

Whilst it is only necessary that the stent graft according to the invention has two sublumens, it is preferred that the stent graft has three or four sublumens. Preferably, those sublumens each comprise at least 20% of the cross-sectional area of the stent graft. By having three or four sublumens, with each of the sublumens subtending a significant cross-sectional fraction, it is comparatively easy to introduce an occlusion device into them, which is of particular relevance during surgery after placement. This is because it will be difficult to accurately manoeuvre the occlusion device to a narrower sublumen. By having a stent graft body having three or four sublumens, with each of them covering a significant portion of the TIPS stent graft's cross-sectional area, introducing the occlusion device into one of those sublumens is fairly easily possible.

Alternatively, it is also preferred if there are at least 6, preferably at least 8, and more preferably at least 10 sublumens. Having such a high number of sublumens, which each having an approximately equal cross-sectional area of the lumen itself, allows for a very accurate adjustment of the cross-sectional area of the stent graft body and hence allows for a very precise treatment of hepatic encephalopathy.

It is also preferred if the stent graft is a self-expanding stent graft which will self expand at body temperature (i.e.

around 37° C.). Such stent grafts are typically made using a memory alloy metal such as nitinol. They will expand upon placement in the patient's body thanks to being warmed by the blood in the patient's bloodstream. Accordingly, a PTA catheter is no longer needed for dilatation, so the placement of the TIPS stent graft is easier.

It is also preferred if the at least one sublumen is formed as a tube which is adhered to an inner surface of the stent body. When forming the sublumen as a tube having preferably a circular cross-section, one has a larger degree of freedom in the design of that tube, compared with the use of membranes extending across the stent graft body lumen.

To keep the tube open, it is preferred that a band extends diametrically across the interior of the tube. This helps in avoiding that the tube collapses.

It is also an option that at least one of the sublumens is formed by a sheet extending from one circumferential position of the stent graft body to another circumferential position of the stent graft body. This sheet thereby separates one sublumen from the remainder of the lumen of the stent graft body. Such a TIPS stent graft is comparatively easy to manufacture.

It is preferred that the cross-sectional area of at least one, preferably all of the sublumens is essentially constant along the length of the respective sublumens. That is, the cross-sectional area does not vary significantly when going from one end of the stent graft to the other end of the stent graft. This ensures that fluid can flow through the stent graft essentially unimpeded unless, of course, the respective sublumen is occluded.

According to another aspect of the invention, there is a kit of parts which comprises the TIPS stent graft as described previously together with an occlusion device. The occlusion device can be placed in one of the sublumens so as to block or at least significantly reduce blood flow through that sublumen. I.e., it is designed to occlude that sublumen. With such a kit of parts, it becomes possible to restrict the blood flow in the TIPS stent graft post-placement.

It is furthermore preferred if the kit of parts additionally comprises a balloon catheter. This balloon catheter is arranged for expanding one or more of the sublumens to adjust the cross-sectional diameter of the hollow stent body which is available for blood flow. This adjustment can, for example occur by expanding a sublumen which is adjacent to the sublumen which is occluded by the occlusion device. Thereby, the occlusion device will be compressed so that, overall, the cross-sectional area available for blood flow is increased. On the other hand, one could also increase in diameter the sublumen which is occluded which would then tend to reduce the cross-sectional area which is available for blood flow. Accordingly, using such a kit of parts, the cross-sectional area available for blood flow can be accurately adjusted.

BRIEF DESCRIPTION OF THE DRAWINGS

FIG. 1 shows a TIPS stent graft according to a first embodiment of the invention.

FIG. 2 shows a TIPS stent graft according to the second embodiment of the invention.

FIGS. 3*a*) and *b*) show TIPS stent grafts according to the third and fourth embodiments of the invention.

DETAILED DESCRIPTION OF THE DRAWINGS

FIG. 1*a*)-*c*) show a TIPS stent graft 10 according to the first embodiment. A TIPS stent graft 10 comprises a stent graft body 12 having an essentially tubular shape. By means of a membrane 17, the inner lumen 14 of the stent graft 10 is separated into first and second sublumens 16, 18. As can be seen from the schematic diagrams, second sublumen 18 has a somewhat smaller cross-sectional diameter and cross-sectional area then first sublumen 16.

Whilst the drawing in FIG. 1*a*) shows the TIPS stent graft when not in use with all of the sublumens 16, 18 open, FIG. 1*b*) shows the TIPS stent graft when the second sublumen 18 is occluded by means of an occlusion device 36. Such an occlusion device can, for example, be in the shape of one or more occlusion spirals. Since blood flow is impeded through the second sublumen 18, the effective cross-sectional area of the TIPS stent graft 10 for blood flow is reduced. As pointed out previously, this can be used for treating hepatic encephalopathy.

FIG. 1*c*) shows yet another use condition of the TIPS stent graft 10 according to the first embodiment. Again, an occlusion device 36 is provided inside the second sublumen 18. However, so as to increase the cross-sectional area of the second sublumen 18, a balloon expandable stent 40 is provided which can be inflated and deflated by means of a catheter (not shown). By means of the balloon expandable stent 40, the cross-sectional area of the second sublumen 18 can be increased to thereby effectively decrease the cross-sectional area of the first sublumen 16 further. This can be used to adjust the cross-sectional area available for blood flow of the TIPS stent graft.

FIG. 2 shows a TIPS stent graft according to the second embodiment of the present invention. It shows a cross-sectional view of such a stent graft, where the cross-section has been taken in a plane perpendicular to the longitudinal axis of the stent graft.

As can be seen, the stent graft body 12 comprises a first sublumen 16 and a second sublumen 18. The stent graft body 12 itself comprises a stent 30 which is covered by an inner ePTFE layer 34 and an outer ePTFE layer 32. Adhered to an inside of the inner ePTFE layer 34 is a tube 15 which serves as the second sublumen 18. Provided on an inside of the tube 15 is a band 26 so as to keep it open. The band 26 is arranged so as to extend between points which are not identical with the point at which the tube 15 is adhered to the inner ePTFE layer 34.

The tube 15 inside the stent craft 12 could be incorporated on the inner surface of the inner ePTFE layer 34 of the stent graft 12 during the covering process of the stent 30 as follows: a tube 15 made of FEP or PTFE is placed inside the inner layer 34 of the covering and over a mandrel during a sintering process of the covering. In order to keep the extra lumen open, a silver band 26 is provided inside the sublumen 18 defined by the tube 15. Then an inner ePTFE layer 34, the stent 30 and the outer ePTFE layer 32 are placed over the mandrel and are then pressed with a PTFE tape material.

Using such an embodiment, during the loading process of the stent graft inside a deployment sheet, the inner catheter of the deployment sheath can be placed inside the sublumen 18 and a loading process can be performed. This has the advantage that a potential guidewire will be inside the sublumen 18 after stent graft deployment. A second guidewire can be placed inside the stent graft 12 in order to balloon the stent to its diameter. After the second balloon has been advanced over the guidewire that is already placed inside the lumen either to just balloon it to open up the lumen or to place the balloon expandable stent.

FIGS. 3*a*) and 3*b*) show the third and the fourth embodiment of the TIPS stent graft according to the present invention.

Turning to FIG. 3*a*) first, a third embodiment of the TIPS stent graft is shown in a cross-section perpendicular to the longitudinal axis of the TIPS stent graft. An inner lumen 14 of the stent graft 12 is separated by means of membrane 17 into first, second, and third sublumens 16, 18, 20. Also indicated are bare stent components 24 which are provided at one longitudinal end of the TIPS stent graft 12 and which will, when implanted, flare out to keep the TIPS stent graft 12 in place.

FIG. 3*b*) shows a TIPS stent graft according to the fourth embodiment. Again, by means of two membranes 17, a lumen of the TIPS stent graft body 12 has been separated into the first, second, third, and fourth sublumens 16, 18, 20, and 22. Again, bare parts 24 of the stent used for the TIPS stent graft are provided at one end of the stent graft.

In both FIGS. 3*a*) and 3*b*), the first to third or first to fourth sublumens 16 to 20 and 16 to 22 can be occluded by means of adequate occlusion devices so as to reduce the effective diameter available for blood to flow through the TIPS stent graft.

The invention claimed is:

1. A kit of parts, comprising:

a Transjugular Intrahepatic Portosystemic Shunt (TIPS) stent graft comprising:

a hollow stent graft body, the hollow stent graft body having a lumen extending between a first longitudinal end and a second longitudinal end to let fluid pass through the hollow stent graft body from the first longitudinal end to the second longitudinal end, the lumen comprising at least two sublumens extending from the first longitudinal end to the second longitudinal end which are separated from one another, wherein a first sublumen is formed as a tube that is adhered to an inner surface of the hollow stent graft body along a length of the tube between the first longitudinal end and the second longitudinal end, the tube comprising a band extending diametrically through an interior of the tube of the first sublumen so as to keep the interior of the tube of the first sublumen open, each of the at least two sublumens capable of being blocked so as to reduce blood flow through the TIPS stent graft; and an occlusion device separate from the TIPS stent graft, the occlusion device being arranged to, when deployed, block blood flow through one of the at least two sublumens thereby restricting blood flow in the TIPS stent graft post-placement.

2. The kit of parts according to claim 1, the TIPS stent graft comprising 3 or 4 sublumens.

3. The kit of parts according to claim 1, the TIPS stent graft comprising at least 10 sublumens.

4. The kit of parts according to claim 1, the TIPS stent graft being a self-expanding stent graft.

5. The kit of parts according to claim 1, wherein the first sublumen of the at least two sublumens is formed by a sheet extending from one circumferential position of the hollow stent graft body to another circumferential position of the hollow stent graft body.

6. The kit of parts according to claim 1, a cross-sectional area of the first sublumen of the at least two sublumens being essentially constant along the length of the first sublumen.

7. The kit of parts according to claim 1, further comprising:

a balloon catheter arranged for expanding the at least two sublumens to thus adjust a cross-sectional diameter of the hollow stent graft body that is available for blood flow, wherein the balloon catheter is separate from the occlusion device.

8. The kit of parts according to claim 1, wherein the hollow stent graft body is formed of a stent that is coated with a coating material of either expanded polytetrafluoroethylene (ePTFE) or fluorinated ethylene propylene (FEP).

9. The kit of parts according to claim 1, wherein the band extends between two points of attachment that are circumferentially spaced apart from a location where the tube is adhered to the inner surface of the hollow stent graft body along the length of the tube.

10. A kit of parts, comprising:

a Transjugular Intrahepatic Portosystemic Shunt (TIPS) stent graft comprising:

a hollow stent graft body, the hollow stent graft body having a lumen extending between a first longitudinal end and a second longitudinal end to let fluid pass through the hollow stent graft body from the first longitudinal end to the second longitudinal end, the lumen comprising at least two sublumens extending from the first longitudinal end to the second longitudinal end which are separated from one another, wherein a first sublumen is formed as a tube that is adhered to an inner surface of the hollow stent graft body along a length of the tube between the first longitudinal end and the second longitudinal end, the tube comprising a band extending diametrically through an interior of the tube of the first sublumen so as to keep the interior of the tube of the first sublumen open, each of the at least two sublumens capable of being blocked so as to reduce blood flow through the TIPS stent graft;

an occlusion device separate from the TIPS stent graft, the occlusion device being arranged to, when deployed, block blood flow through one of the at least two sublumens thereby restricting blood flow in the TIPS stent graft post-placement; and a balloon catheter arranged for expanding the at least two sublumens to thus adjust a cross-sectional diameter of the hollow stent graft body that is available for blood flow, wherein the balloon catheter is separate from the occlusion device.

11. The kit of parts according to claim 10, the TIPS stent graft comprising 3 or 4 sublumens.

12. The kit of parts according to claim 10, the TIPS stent graft comprising at least 10 sublumens.

13. The kit of parts according to claim 10, the TIPS stent graft being a self-expanding stent graft.

14. The kit of parts according to claim 10, wherein the first sublumen of the at least two sublumens is formed by a sheet extending from one circumferential position of the hollow stent graft body to another circumferential position of the hollow stent graft body.

15. The kit of parts according to claim 10, a cross-sectional area of the first sublumen of the at least two sublumens being essentially constant along the length of the first sublumen.

16. The kit of parts according to claim 10, wherein the occlusion device comprises an embolization coil.

17. The kit of parts according to claim 10, wherein the hollow stent graft body is formed of a stent that is coated with a coating material of either expanded polytetrafluoroethylene (ePTFE) or fluorinated ethylene propylene (FEP).

18. The kit of parts according to claim 10, wherein the band extends between two points of attachment that are circumferentially spaced apart from a location where the tube is adhered to the inner surface of the hollow stent graft body along the length of the tube.

* * * * *